United States Patent
Strupat et al.

(10) Patent No.: US 6,358,058 B1
(45) Date of Patent: Mar. 19, 2002

(54) AEROSOL DISPENSING INHALER TRAINING DEVICE

(75) Inventors: John P. Strupat; Alex M. W. Verdun, both of London (CA)

(73) Assignee: 1263152 Ontario Inc., London (CA)

( * ) Notice: Subject to any disclaimer, the term of this patent is extended or adjusted under 35 U.S.C. 154(b) by 0 days.

(21) Appl. No.: 09/016,756

(22) Filed: Jan. 30, 1998

(51) Int. Cl.$^7$ ............................................. G09B 23/28
(52) U.S. Cl. ...................................... 434/262; 434/267
(58) Field of Search .............................. 434/262, 267, 434/84; 128/200.12, 200.14, 200.23, 200.24, 905; 600/538; 364/413.01

(56) References Cited

U.S. PATENT DOCUMENTS

| | | |
|---|---|---|
| 2,284,013 A | 5/1942 | Pardoe |
| D182,004 S | 1/1958 | Spreitzer |
| D218,934 S | 10/1970 | Cordero et al. |
| 3,626,755 A | 12/1971 | Rudolph |
| 3,681,986 A | 8/1972 | Wyatt |
| 3,719,083 A | 3/1973 | Morris et al. |
| 3,722,278 A | 3/1973 | Young et al. |
| 4,050,303 A | 9/1977 | Hemp et al. |
| 4,078,428 A | 3/1978 | Baker et al. |
| 4,196,621 A | 4/1980 | Beese et al. |
| 4,244,230 A | * 1/1981 | Bauer ....................... 73/861.19 |
| 4,308,755 A | * 1/1982 | Millar ...................... 73/861.77 |
| 4,363,238 A | 12/1982 | William |
| 4,420,983 A | * 12/1983 | Langdon ................... 73/861.18 |
| 4,481,828 A | 11/1984 | Cheng |
| 4,484,577 A | * 11/1984 | Sackner .................. 128/203.28 |
| 4,495,944 A | 1/1985 | Brisson et al. |
| D278,316 S | 4/1985 | Bengtson |
| 4,523,479 A | * 6/1985 | Johnson ................... 73/861.35 |
| 4,546,793 A | 10/1985 | Stupecky |
| 4,558,710 A | 12/1985 | Eichler |

(List continued on next page.)

FOREIGN PATENT DOCUMENTS

| | | |
|---|---|---|
| DE | 29 41 426 | 2/1981 |
| FR | 2 701 399 | 8/1994 |
| WO | WO 87/04354 | 7/1987 |
| WO | WO 97/13553 | 4/1997 |

*Primary Examiner*—Jacob K. Ackun, Jr.
*Assistant Examiner*—Kurt Fernstrom
(74) *Attorney, Agent, or Firm*—Brinks Hofer Gilson & Lione

(57) ABSTRACT

An aerosol dispensing inhaler training device for determining whether a user is properly operating an aerosol dispensing device. The training device includes an aerosol dispensing device having a container with a valve stem extending longitudinally therefrom and movable between a closed position and an open position. The container dispenses a portion of the contents within the container when the valve stem is moved to the open position. The aerosol dispensing device includes a housing adapted to support the container reciprocally moveable within the housing along a longitudinal axis from a first position, the housing comprising a well adapted to receive the valve stem and an exhaust port comprising one end in fluid communication with the well and a second end in fluid communication with the ambient atmosphere, wherein the portion of the contents within the container is dispensed from the first end of the exhaust port to the second end of the exhaust port when the housing moves to an actuation position where the valve stem is actuated so that a portion of the contents within the container is dispensed through the second end of the exhaust port when the valve stem is moved to the open position. An actuation sensor generates a signal that indicates when the housing is moved to the actuation position and the valve stem is actuated. A shake sensor determines whether the contents within the container have been properly agitated for consumption by a user.

14 Claims, 11 Drawing Sheets

U.S. PATENT DOCUMENTS

| | | | |
|---|---|---|---|
| 4,570,493 A | * | 2/1986 | Leembuis ................ 73/861.62 |
| D296,530 S | | 7/1988 | Nowacki et al. |
| 4,817,822 A | | 4/1989 | Rand et al. |
| 4,961,344 A | | 10/1990 | Rodder |
| 4,984,158 A | * | 1/1991 | Hillsman ................ 364/413.04 |
| 4,989,456 A | | 2/1991 | Stupecky |
| 5,005,582 A | * | 4/1991 | Serikov ...................... 128/691 |
| 5,020,527 A | | 6/1991 | Dessertine |
| 5,033,312 A | | 7/1991 | Stupecky |
| 5,038,621 A | | 8/1991 | Stupecky |
| 5,167,506 A | * | 12/1992 | Kilis .......................... 434/262 |
| 5,233,998 A | | 8/1993 | Chowienczyk et al. |
| 5,277,195 A | | 1/1994 | Williams |
| 5,279,163 A | | 1/1994 | D'Antonio et al. |
| 5,284,133 A | | 2/1994 | Burns et al. |
| 5,313,955 A | | 5/1994 | Rodder |
| 5,331,953 A | | 7/1994 | Andersson et al. |
| 5,333,106 A | * | 7/1994 | Lanpher ................ 364/413.01 |
| 5,363,691 A | * | 11/1994 | Gallagher .................. 73/32 A |
| 5,383,470 A | | 1/1995 | Kolbly |
| 5,415,161 A | | 5/1995 | Ryder |
| 5,487,378 A | * | 1/1996 | Robertson ............. 128/200.16 |
| 5,505,192 A | | 4/1996 | Samiotes et al. |
| 5,655,516 A | | 8/1997 | Goodman et al. |
| 5,676,129 A | * | 10/1997 | Rocci .................... 128/200.23 |
| 5,692,492 A | | 12/1997 | Bruna et al. |
| 5,809,997 A | | 9/1998 | Wolf |

\* cited by examiner

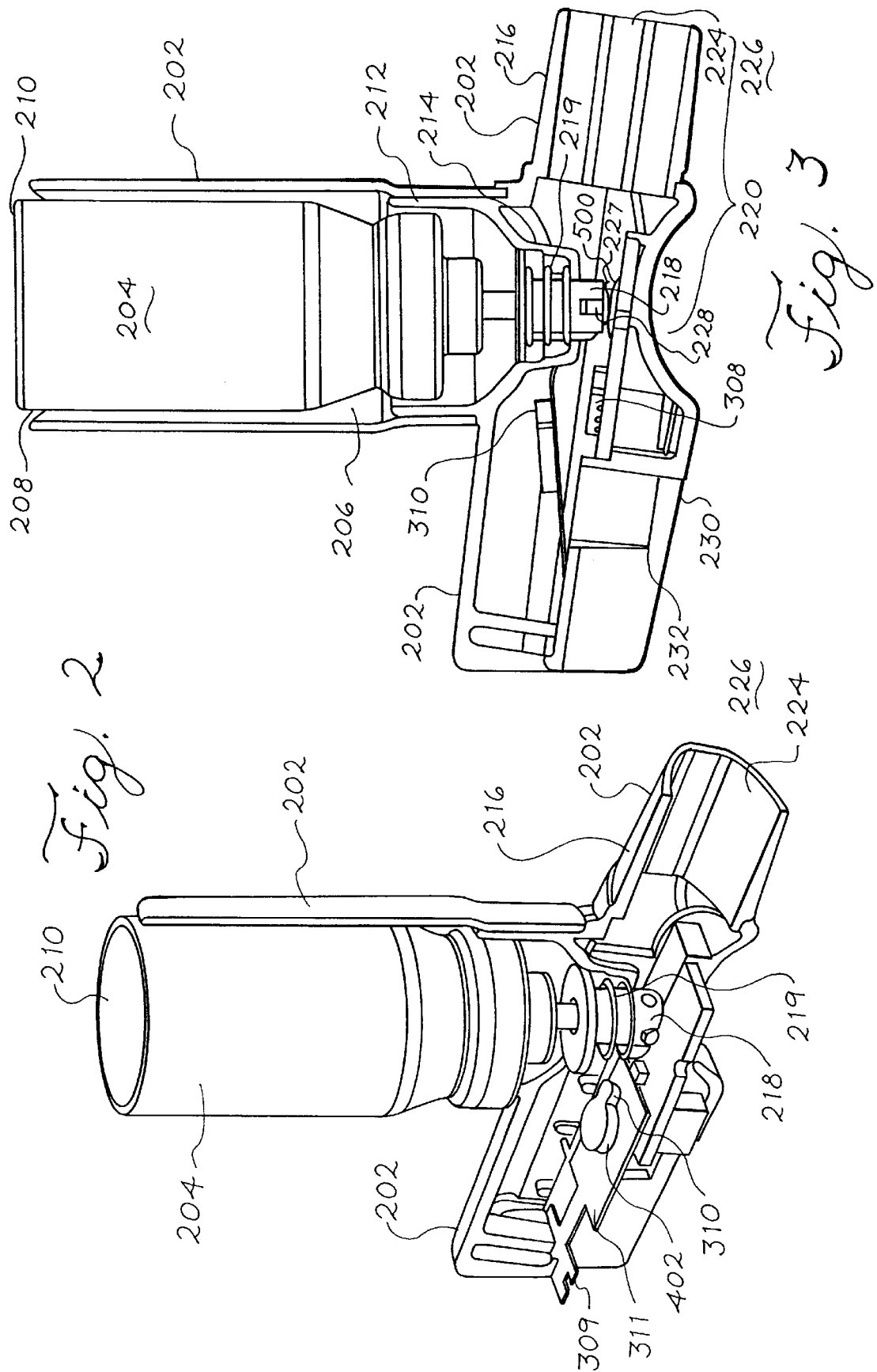

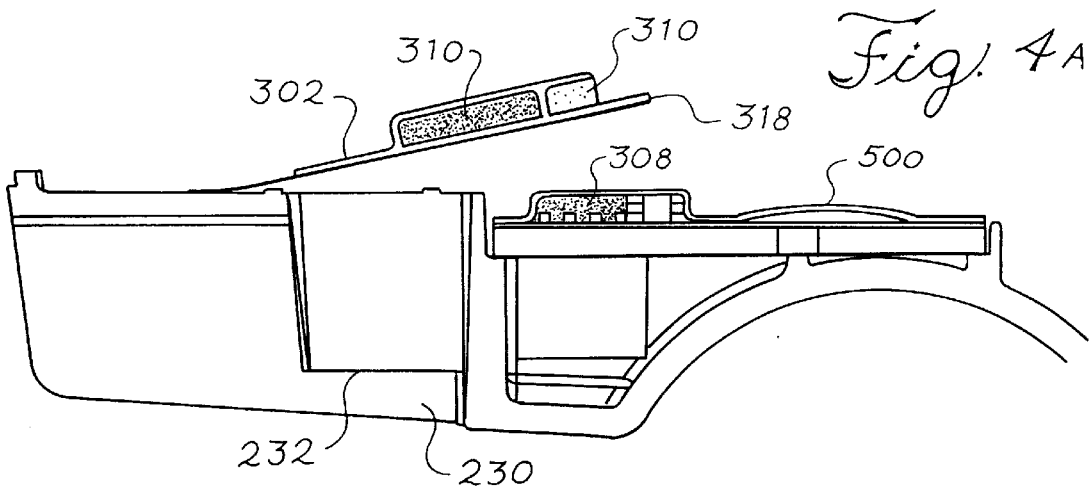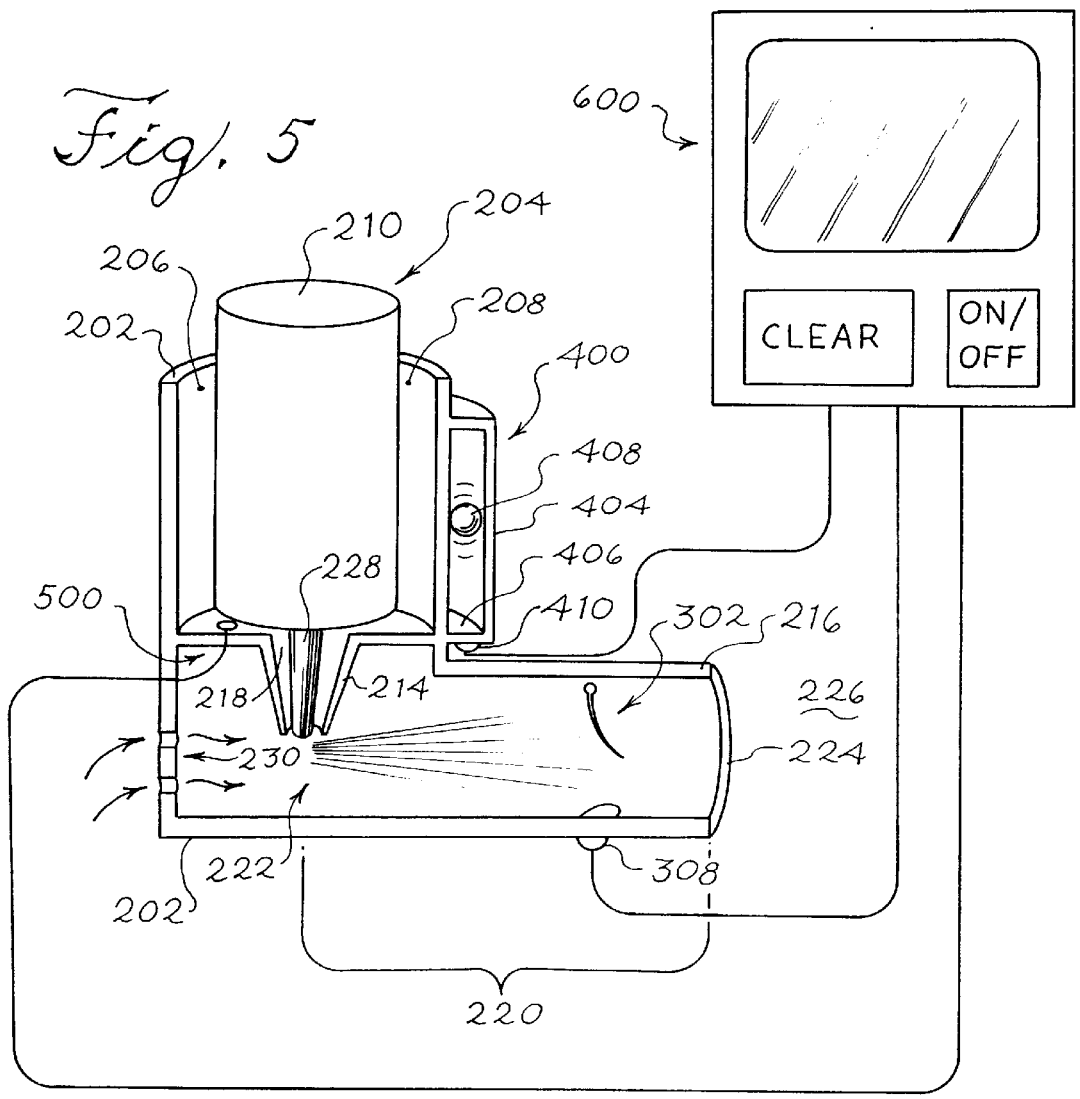

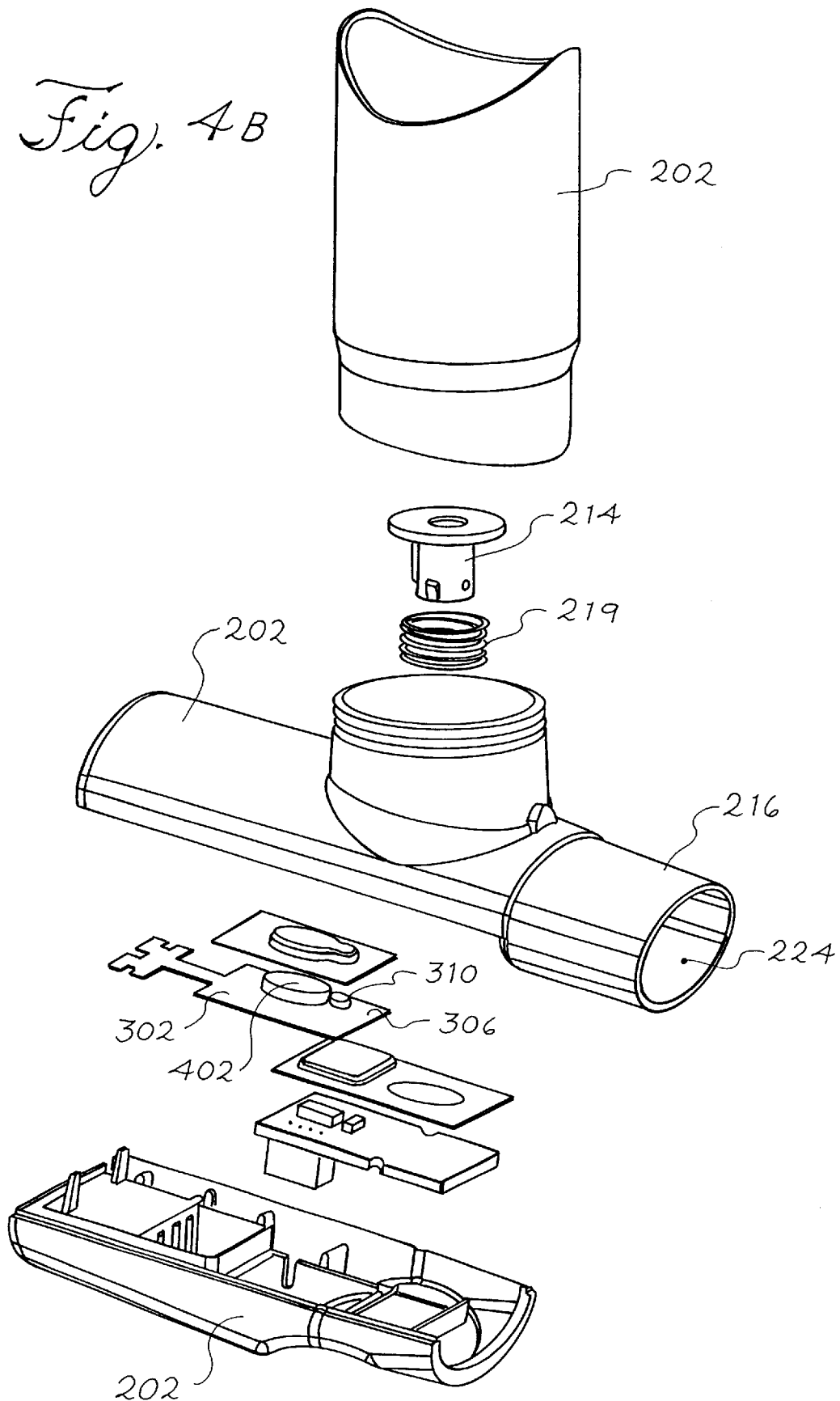

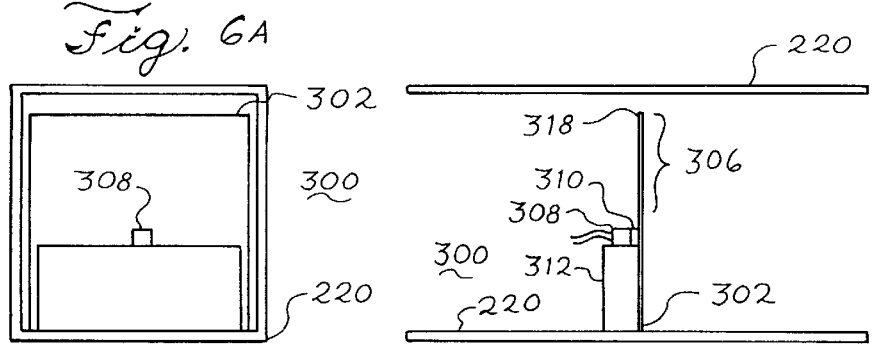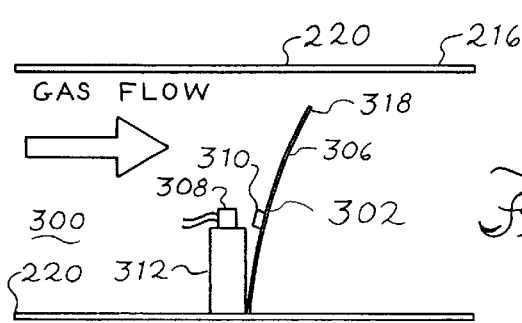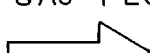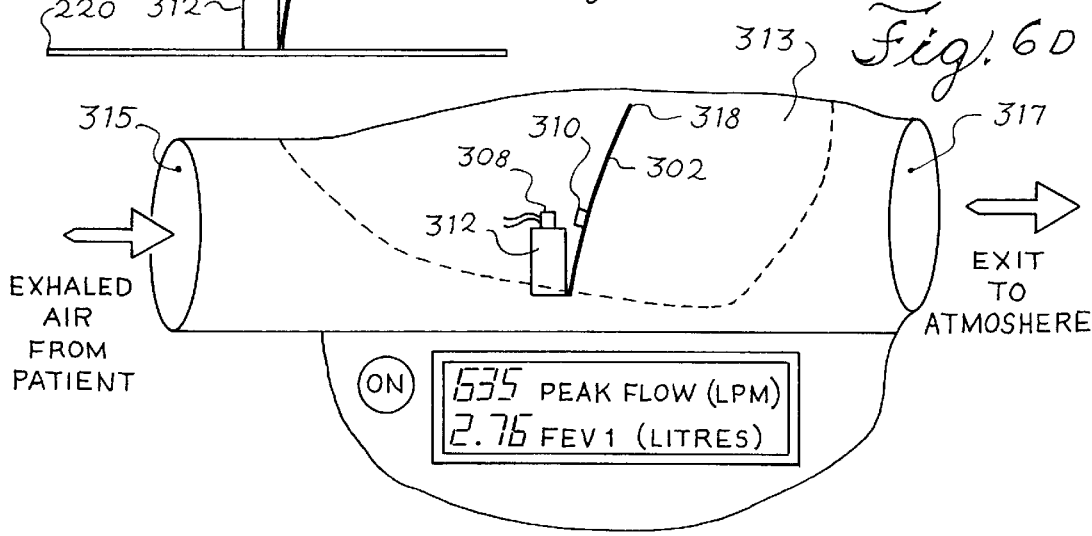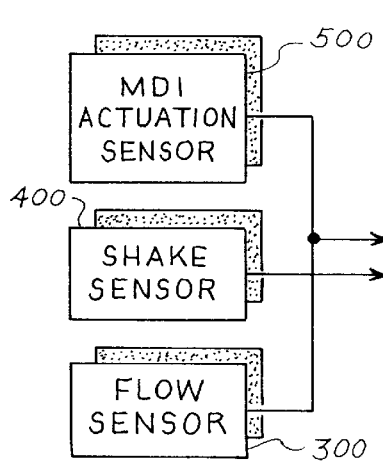

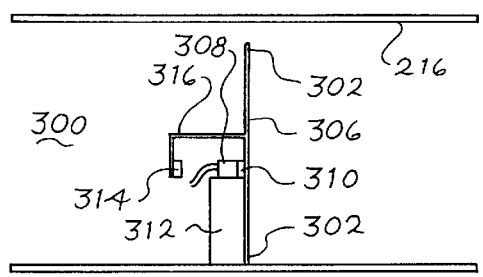
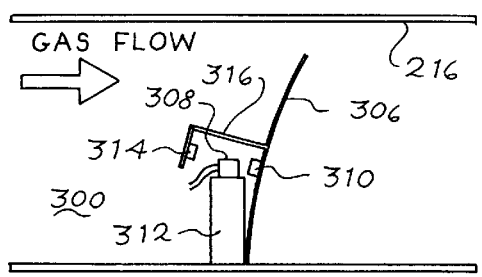
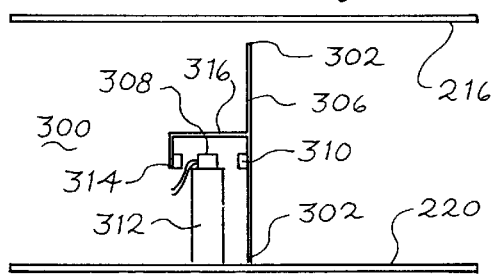
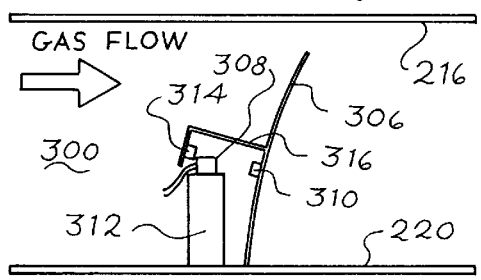
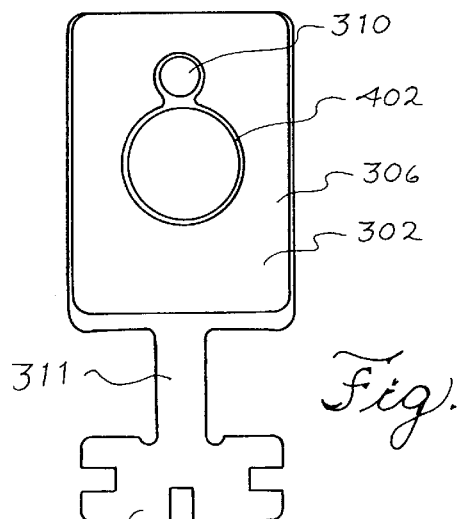
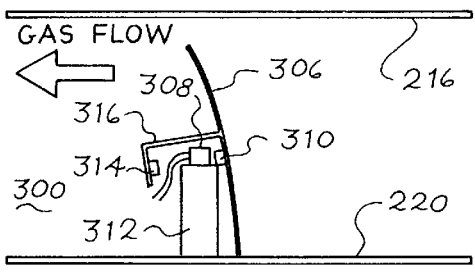
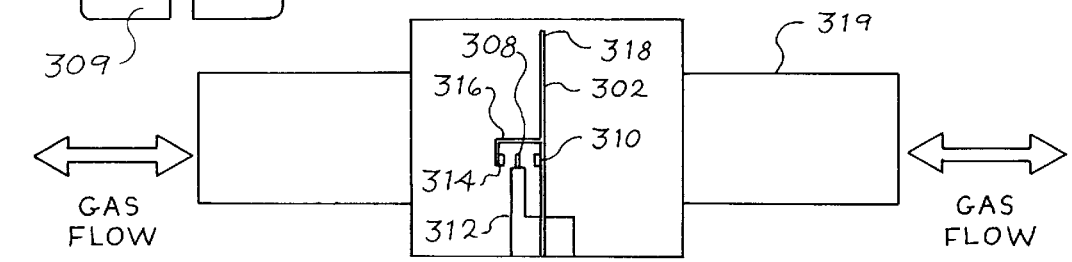

AIR

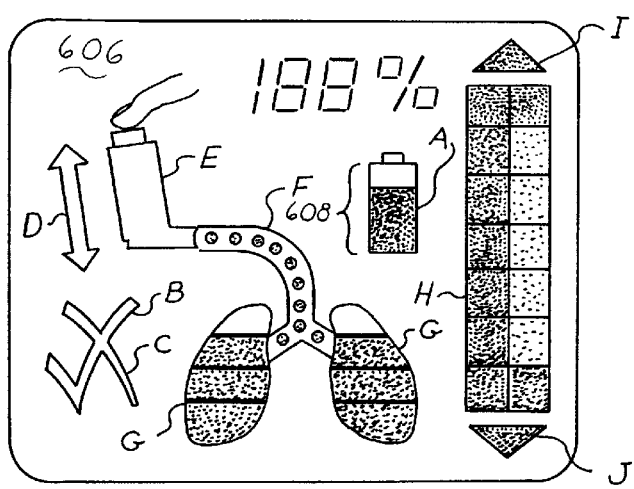
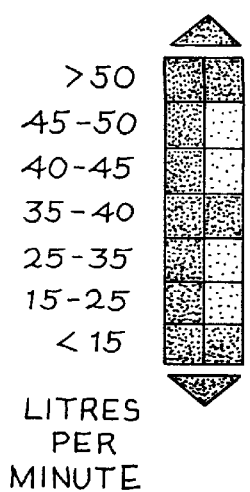
Fig. 14
Fig. 15
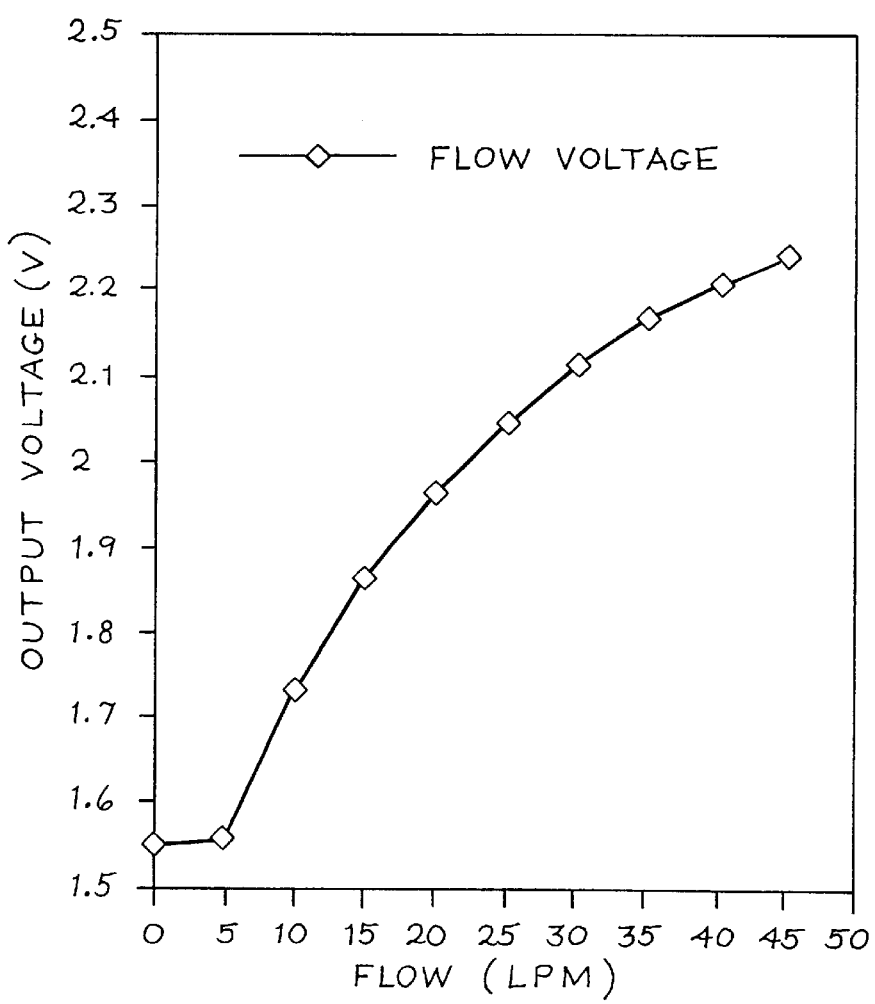
Fig. 11A

AEROSOL DISPENSING INHALER TRAINING DEVICE

BACKGROUND OF THE INVENTION

1. Field of the Invention

The present invention relates generally to an aerosol dispensing inhaler training device, and in particular, to an aerosol dispensing inhaler training device that can monitor several parameters, such as the flow rate, shaking of the container and the activation of the container comprising a solution or suspension which upon actuation transforms into an aerosol.

2. Description of Related Art

Aerosol administered medication for bronchial therapy in such conditions as asthma, chronic bronchitis and emphysema is generally the preferred dosage technique for reasons of efficacy, reduced side effects and economy. Such particulate drugs are commonly prescribed using metered dose inhaler (MDI) type devices. It is well recognized that improper inhalation technique in the use of MDI devices is a serious barrier to effective therapy.

Some patients may have difficulty in the use of conventional MDI devices especially in terms of controlling inhalation, and proper activation timing of the MDI delivery system. For example, patients may inhale too fast, or in an erratic manner. Another common problem is that patients may delay activation of the MDI device until after inspiration has started, and therefore, the crucial initial portion of the inspired breath does not contain medication. After activation, patients may frequently begin their MDI inspiration breaths at improper levels of lung volume, for example, their lungs may already be relatively full of air and therefore a proper large volume of inspired air is impossible.

Once the proper MDI inspiration breath has been achieved, it is important for the patient to sustain a brief period of breath holding so that the medicated mist is properly deposited in the airways of the patient.

The desired time interval of breath holding is generally thought to be about five to ten seconds. However, this desirable time may be functionally limited, as dictated by individual patient needs and breath holding capabilities.

While it is generally felt the timing of MDI activation should be simultaneous with the beginning of inspiration, there is some scientific opinion that questions whether said activation should be a fraction of a second before or after the beginning of inspiration. However, it is understood that these events are substantially concurrent.

It should be apparent from the above, that while the act of using an MDI device may appear simple, it can be in fact a complex act, and the proper performance of this technique is crucial to the optimal delivery of drugs to the bronchial airways. Without proper MDI inhalation technique, the patient may in fact derive little or no benefit from this form of drug therapy.

In this vein, there have been attempts in the past to measure the magnitude of the flow rate and the timing of the dispensing of the aerosol along with improving the training of individuals to use a proper MDI inhalation technique. In the case of measuring the flow rate, many techniques have been used in the past ranging from pressure differential techniques (i.e., pneumotachs that measure pressure drop across a time meshed screen with a linear resistance, a bundle of capillary tubes with a linear resistance, a fixed orifice or a flexible orifice) to mechanical techniques (i.e., spinning turbines, paddle wheels, hinged flaps with potentiometers) to ultrasonic techniques (i.e., time of flight pulses). One disadvantage to the above flow rate techniques, except the ultrasonics technique, is that the liquid particles present in a patient's exhaled gas can contaminate the flow rate devices to the extent that they produce inaccurate readings. The ultrasonics technique suffers the drawback that it requires relatively expensive piezoelectric elements and complex signal analysis that limits widespread application.

In the case of teaching proper usage of a metered dose inhaler, past devices and systems have omitted teaching the proper technique for shaking the aerosol container prior to inhalation.

SUMMARY OF THE INVENTION

One aspect of the present invention regards an aerosol dispensing inhaler training device for determining whether a user is properly operating an aerosol dispensing device. The training device includes an aerosol dispensing device having a container with a valve stem extending longitudinally therefrom and movable between a closed position and an open position. The container dispenses a portion of the contents within the container when the valve stem is moved to the open position. The aerosol dispensing device includes a housing adapted to support the container reciprocally moveable within the housing along a longitudinal axis from a first position, the housing comprising a well adapted to receive the valve stem and an exhaust port comprising one end in fluid communication with the well and a second end in fluid communication with the ambient atmosphere, wherein said portion of the contents within the container is dispensed from the first end of the exhaust port to the second end of the exhaust port when the housing moves to an actuation position where the valve stem is actuated so that a portion of the contents within the container is dispensed through the second end of the exhaust port when the valve stem is moved to the open position. An actuation sensor generates a signal that indicates when the container is moved to the actuation position and the valve stem is actuated. A shake sensor determines whether the contents within the container have been properly shaken for consumption by a user.

A second aspect of the present invention regards a method of training an individual on how to properly use an aerosol dispensing device. The method includes providing an aerosol dispensing inhaler training device with a container, agitating the contents of the container, determining whether the contents of the container have been properly agitated during the agitating step for consumption by an individual; and repeating the previous steps if it is determined that during the agitating step that the contents of the container have not been properly agitated for consumption by an individual.

The present invention provides significant advantages over other aerosol dispensing inhaler training devices. In particular, several aspects of the present invention's use of a flow rate measurement device with reduced risk of being contaminated by a patient's exhaled gas while at the same time having a simple and economical structure.

Another advantage of several aspects of the present invention is that it regards a device and method for teaching the proper technique for shaking a container prior to inhalation.

The present invention, together with further objects and advantages, will be best understood by reference to the following detailed description taken in conjunction with the accompanying drawings.

BRIEF DESCRIPTION OF THE DRAWINGS

FIG. 2 shows a perspective cut away view of an aerosol dispensing device to be used with the aerosol dispensing training devices of FIG. 1;

FIG. 3 shows a cross-sectional view of the aerosol dispensing device of FIG. 2;

FIG. 4A shows a side cross-sectional view of the aerosol dispensing device of FIG. 2;

FIG. 4B shows an exploded perspective view of the aerosol dispensing device of FIG. 2;

FIG. 5 schematically shows a partial cross-sectional view of a second embodiment of an aerosol dispensing training device according to the present invention;

FIG. 6A shows a front view of a first embodiment of a flow rate measurement device at a resting position according to the present invention;

FIG. 6B shows a side view of the flow rate measurement device of FIG. 6A at a resting position;

FIG. 6C shows a side view of the flow rate measurement device of FIG. 6A when a gas is flowing;

FIG. 6D schematically shows a spirometer that employs the flow rate measurement device of FIGS. 6A–C;

FIG. 7A shows a side view of a second embodiment of a flow rate measurement device at a resting position according to the present invention;

FIG. 7B shows a side view of the flow rate measurement device of FIG. 7A when a gas is flowing;

FIG. 8A shows a side view of a third embodiment of a flow rate measurement device at a resting position according to the present invention;

FIG. 8B shows a side view of the flow rate measurement device of FIG. 8A when a gas is flowing in one direction;

FIG. 8C shows a side view of the flow rate measurement device of FIG. 8A when a gas is flowing in a direction opposite to the flow of FIG. 8B;

FIG. 8D schematically shows a life support ventilator that employs the flow rate measurement device of FIGS. 8A–C;

FIG. 10 shows a top view of an embodiment of a vane to be used with the flow rate measurement devices of FIGS. 2–4;

FIG. 11A shows an example of the flow rate or flowage measured by the flow rate measurement devices of FIGS. 6–9;

FIG. 13 schematically shows an embodiment of a processor to be used with the aerosol dispensing inhaler training device of FIGS. 1–5;

FIG. 14 schematically shows an embodiment of a display to be used with the aerosol dispensing inhaler training device of FIGS. 1–5;

FIG. 15 schematically shows an embodiment of a bar graph to be used with the display of FIG. 14.

DETAILED DESCRIPTION OF THE PRESENTLY PREFERRED EMBODIMENTS

Figure 1:
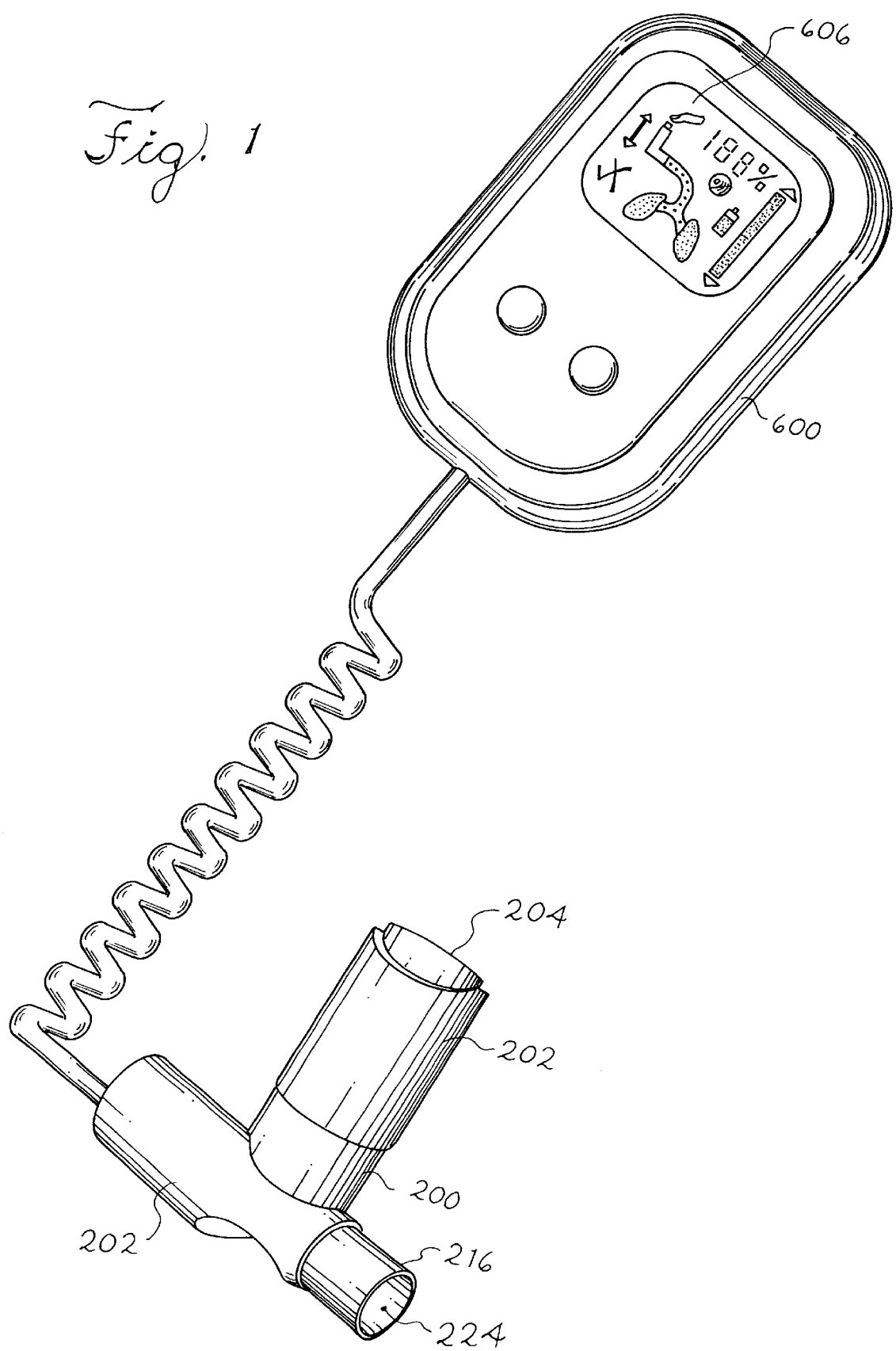
FIG. 1 schematically shows a top view of an aerosol dispensing inhaler training device according to the present invention.

An aerosol dispensing inhaler training device 100 according to the present invention is schematically shown in FIGS. 1–17, wherein like elements are identified by like numerals. As described below, the aerosol dispensing inhaler training device 100 is basically made of 5 major components: 1) the aerosol dispensing device 200, 2) the flow rate measurement device 300, 3) the shaking sensor 400, 4) the actuation sensor 500, and 5) the monitoring device 600. Each of these components is discussed below:

A. Aerosol Dispensing Device

FIGS. 1–5 show an aerosol dispensing device 200 that includes a T-shaped housing 202 and a cylindrical container 204 disposed therein. The housing 202 has a longitudinally extending cylindrical cavity 206 shaped to receive the container. A top portion of the housing 202 is generally open such that the container 204 can be inserted into the housing 202 through opening 208 and be installed therein with a bottom end 210 of the container 204 protruding from the housing 202 and exposed to the user for actuation.

The term "longitudinal" as used herein is intended to indicate the direction of the reciprocal movement of the container 204 relative to the housing 202. The terms "top," "bottom," "upwardly" and "downwardly" are intended to indicate directions when viewing the aerosol dispensing device 200 as shown in FIGS. 2–4, but with the understanding that the container 204 is inverted such that the top surface thereof is located adjacent the bottom of the housing 202 and vice versa.

As shown schematically in FIGS. 2 and 4B, a cylindrical support block 212 having a movable well 214 is formed in a bottom portion 216 of the housing 202. The movable well 214 is cylindrical in shape and is inserted into an orifice 218 that penetrates the support block 212 to communicate with a bottom portion of the movable well 214. A spring 219 is also placed in the orifice 218 so that it surrounds the movable well 214. The spring 219 acts to maintain the well 214 and the container 204 away from an actuation position to be described below. A mouthpiece 216, intended for insertion into the mouth of a patient, forms an exhaust port 220 that has one end 222 in fluid communication with the movable well 214 and a second end 224 in fluid communication with the ambient atmosphere 226. The exhaust port 220 has a length of approximately 3.5 cm and an oval-like cross-section with a maximum width of approximately of 2.2 cm and a maximum height of approximately 1.5 cm. Of course, the exhaust port 220 may have other shapes, such as cylindrical or rectangular, without departing from the spirit of the invention. The mouthpiece 216 extends laterally from the housing 202 so as to facilitate insertion of the mouthpiece into the mouth of the patient.

The cylindrical container 204 has a valve stem 228 extending longitudinally from the bottom end 230 of the container 204. The valve stem 228 extends coaxially from the container 204 and is biased outwardly therefrom by the spring 219 mounted within the container 204. The container 204 is mounted in the housing 202 by press fitting the valve stem 228 in the well 214 of the support block 212.

In a preferred embodiment, the interior of the container 204 is filled with a pressurized propellant and a placebo solution or suspension which is dispensed therefrom in specific metered doses by depressing or moving the valve stem 228 from an extended closed position to a depressed open position. A single metered dose is dispensed from the container 204 by each reciprocal, longitudinal movement of the valve stem 228.

In operation, the opening of the valve stem 228 is effected by moving the container 204 reciprocally within the housing 202 along a longitudinal axis, defined by the valve stem 228 and the reciprocal movement of the container 204, by depressing the exposed bottom end 210 of the container 204 relative to the housing 202 so as to move the valve stem 228 and the movable well 214 against the spring 219 to the open or actuation position as it is supported within the well by the support block 212. As the well 214 is moved to an actuation position where the valve stem 228 is moved to the open position, the container 204 dispenses a portion of the propellant and the placebo solution or suspension within the container 204 through the well 214 and orifice 218. A placebo aerosol is formed within the exhaust port 220. The patient inhales the placebo aerosol and the air within the exhaust port 220 from the first end 222 of the exhaust port 220 to the second end 224 of the exhaust port 220 so that the placebo aerosol is transmitted to the patient through the mouthpiece 216. A grill 230 is formed in the bottom rear end 222 of the aerosol dispensing device 200 so as to allow ambient air to be sucked through the grill and into a rectangular opening 232 that is formed in the aerosol dispensing device 200 so as to be directly underneath the vane 302. The grill 230 has three longitudinal slats that are parallel to one another and separated from one another by approximately 0.2 cm so as to prevent particles larger than 0.2 cm from entering the exhaust port 220. The rectangular opening 232 has a length of approximately 0.9 cm and a width of approximately 1.3 cm.

B. Flow Rate Measurement Device

One of the problems encountered by users of aerosol dispensing devices in general is that the medication may not be inhaled properly. Accordingly, the aerosol dispensing inhaler training device 100 includes a flow rate measurement device 300 that is capable of measuring the flow rate of aerosol through the aerosol dispensing device 200. As shown in FIG. 2, the flow rate measurement device 300 preferably is attached to the interior surface of the exhaust port 220 so as to be positioned between the well 214 and the rear end 222 of the aerosol dispensing device 200. Such a position is preferred because it reduces the amount of aerosol and placebo deposited on the flow rate measurement device 300 and so the flow rate measurement device is able to measure the inhalation flow without impeding the flow of the aerosol which leads to more accurate measurements of the flow rate within the exhaust port 220 when a patient inhales through the mouthpiece 216.

An embodiment of such a flow rate measurement device 300 is schematically shown in FIGS. 6A–C. In particular, the flow rate measurement device 300 has two main components: a movable vane 302 and a sensor 308. The base 309 of the movable vane 302 is secured by the top and bottom of the interior surface of the housing by being clamped therebetween (see FIG. 2). Alternatively, the base 309 can be attached to the bottom of the interior surface of the exhaust port 220 by a well known adhesive. As shown in FIG. 10, the vane 302 has a thickness of approximately 0.05 cm and a rectangular upper section 306 that has a length of approximately 1.9 cm and a width of approximately 1.35 cm. The base 309 has a length of approximately 0.5 cm and a width of approximately 1.2 cm and is integrally attached to a rectangular neck 311 that has a length of approximately 0.65 cm and is integrally attached to the upper section 306. The vane 302 is made of a spring-like material, such as stainless steel. Of course, other shapes for the vane 302 and the upper section 306 are possible without departing from the spirit of the invention. When the patient is not inhaling through the exhaust port 220, the vane 302 stands vertically at a resting position shown in FIG. 6B. When the patient inhales at the mouthpiece 216, the vane 302 pivots or bends so that the upper section 306 is deflected towards the mouthpiece 216 in the direction of the flow of the placebo aerosol and/or inhaled air as shown in FIG. 6C. Note that the vane 302 preferably bends only when the patient inhales and not when the placebo aerosol is dispensed. However, there may be instances where the vane 302 is positioned within the flow path and/or has its spring constant adjusted so that it is deflected when the aerosol placebo is also dispensed. In that case, the vane 302 should occlude approximately 50% of the area impinged by the flow where the vane 302 is located.

Two examples of where the vane 302 is positioned within the flow path is shown in FIGS. 5 and 6D. FIG. 6D shows the vane 302 being used as a flow sensor for a basic pulmonary function spirometer 313. Spirometry is the measurement of lung function and is highly dependent on patient effort. To measure the various lung capacities for volume and flow, the patient exhales at end 315 which causes the exhaled air to deflect the vane 302 and then the exhaled air leaves through the exit end 317 to the atmosphere. From the deflection of the vane 302, a microprocessor can calculate and display such parameters as the peak flow and the FEV1 value. The test results may be compared against accepted norms for individuals with similar height, weight, age and sex. Of course, the spirometer 313 may incorporate automated analysis of results, allow entry of patient data, transmit results electronically, etc.

The application of the vane 302 would be used for direct flow measurement and integrate this information for presentation of volume data. Prior art using other flow sensing methods are more expensive or delicate than this invention. The invention is robust and unaffected by contamination with aerosols from the patient's exhaled gas, by exposure to liquids or cleaning solutions.

The amount of movement or deflection of the upper section 306 of the vane 302 is a measure of the flow rate or flowage within the exhaust port 220. A magnetic sensor 308, such as a Hall element or a magneto-resistive element, is used to measure the movement or deflection of the upper section 306 of the vane 302 from the rest position of FIG. 6B to the deflected position of FIG. 6C. In particular, the sensor 308 measures the deflected position by detecting the magnetic field strength generated by a magnetic element, such as a high energy permanent magnet 310 or an electromagnet, at that position and generating a signal corresponding to the amount of movement of the movable vane 302. The magnetic element 310 is attached to the upper section 306 and preferably is a permanent magnet, such as a type II Neodymium-Iron-Boron (NeFeB) magnet. The magnetic field produced by the permanent magnet preferably is unaffected by moisture, liquids and external magnetic fields and is relatively stable over temperature and time. One way to protect the magnetic element 310 from the environment is to place a thin plastic, such as polyester, over the magnetic element 310.

As shown in the embodiment of FIGS. 6A–D, the sensor 308 is attached to the top of a support 312 that is itself attached to the interior surface of the exhaust port 220. The sensor 308 is positioned above the interior surface of the exhaust port 220 and is adjacent to magnetic element 310 at the rest position shown in FIG. 6B. Like the vane 302, a protective layer of thin plastic can be placed over the sensor 308 to protect it from the environment.

A second embodiment of a flow rate measurement device 300 is shown in FIGS. 7A–B where the flow rate measurement device 300 of FIGS. 6A–C is altered by adding a second magnetic element 314 that is spaced from the sensor 308 by approximately 2 mm at the rest position shown in FIG. 7A. The magnetic element 314 is attached to the vane 302 via an arm 316.

As shown in FIGS. 8A–8D, a third embodiment of a flow rate measurement device 300 is a variation of the flow rate measurement device 300 of FIGS. 7A–B where the vane 302 is offset from the support 312 by approximately 1 mm at the rest position. This results in the magnetic element 310 being spaced from the sensor 308 at the rest position by approximately 1 mm. As shown in FIGS. 8B and 8C, offsetting the vane 302 allows the flow rate measurement device 300 to measure the flow rate in two directions and to determine which direction the flow is moving within the exhaust port 220. This provides the advantage of sensing the flow rate when the user exhales into the exhaust port 220.

An example of the use of a bi-directional sensor is shown in FIG. 8D where the vane 302 is used as a flow sensor in a section of a life support ventilator circuit 319. The ventilator circuit is the common descriptor for the tubing, connectors and other components that confine and direct gas from a ventilator to the patient, and potentially back again. It is well known that a ventilator, or other life support or breathing assist device, acts to provide air or air with additional oxygen, plus humidity, at breathing rates and volumes sufficient to maintain or support life or provide assistance in breathing. As shown in FIG. 8D, the vane 302 (approximate length 3 inches, approximate mass 20 grams) is positioned to measure flow to and from the patient. The signals from the deflection of the vane 302 may be used to integrate the flow data to produce a gas volume that can be displayed on a monitor or sent to other locations. Once patient is through with the ventilator, the vane 302 can be either entirely disposable or partially disposable so that a cleaner vane 302 can be used for the next use.

Figure 9A:
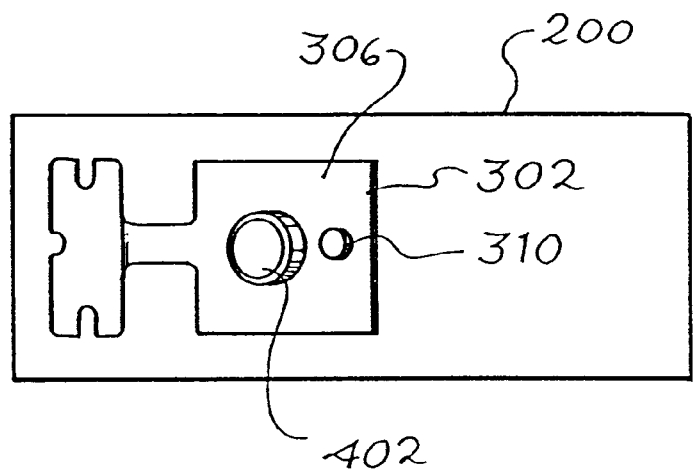
FIG. 9A schematically shows a top view of a fourth embodiment of a flow rate measurement device to be used with the aerosol dispensing device of FIGS. 2–4.
Figure 9B:
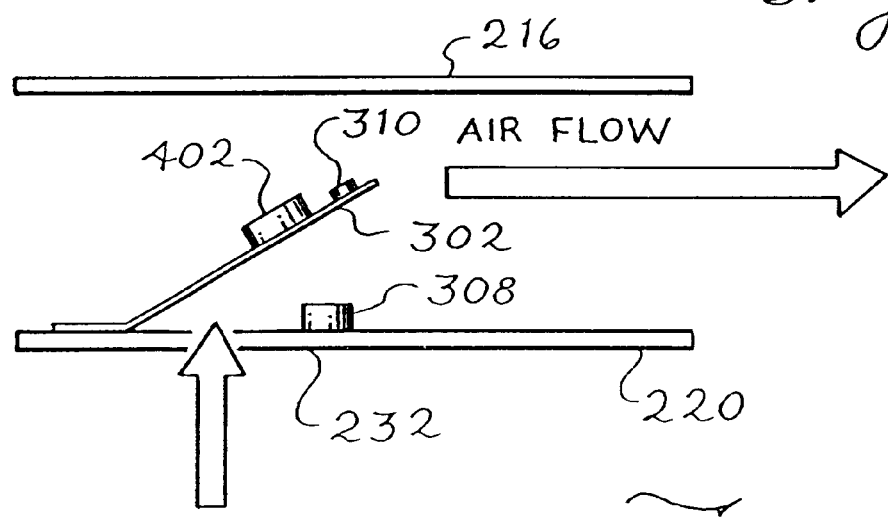
FIG. 9B schematically shows a side view of the flow rate measurement device of FIG. 9A.

A fourth embodiment of a flow rate measurement device 300 is shown in FIGS. 9A–B. In this preferred embodiment, the vane 302 is oriented horizontally rather than vertically as in FIGS. 6–8 so that the free end 318 points toward the mouth piece 216 and along the flow of the gas. In this embodiment, the magnetic element 310 is attached to the top surface of the vane 302 so as to be approximately 0.375 cm from the free end 318 and approximately 0.675 cm from either of the side edges 320 of the vane 302. The sensor 308 is attached to bottom platform 322 so as to face the bottom of the vane 302. When there is no flow, the bottom surface of the vane 302 may be either adjacent to the sensor 308 or may be preloaded so that it is spaced approximately 0.6 cm from the sensor 308.

Note that several variations of the flow rate measurement devices 300 of FIGS. 6–9 are possible. For example, the sensor 308 could be attached to the vane 302 and the magnetic element 310 could be mounted on the support 312 or mounted on or in the interior wall of the exhaust port 220. Another variation is to preload or stress the vane 302 so that a minimum gas flow is required to cause deflection of the vane 302.

The spring-like characteristics of the vanes 302 of FIGS. 6–9 can be altered to meet specific requirements for specific applications. For example, the aerosol dispensing device can be enlarged for larger animals, like horses, or reduced in size for children. For each new application, the spring-like characteristics of the vane 302 can be optimized for deflection distance, physical size, resistance to airflow (back pressure) and vane material selection. In the case of being used for large animals, the vane 302 would be large and thick while the vane 302 for children would be small and thin.

Figure 11B:
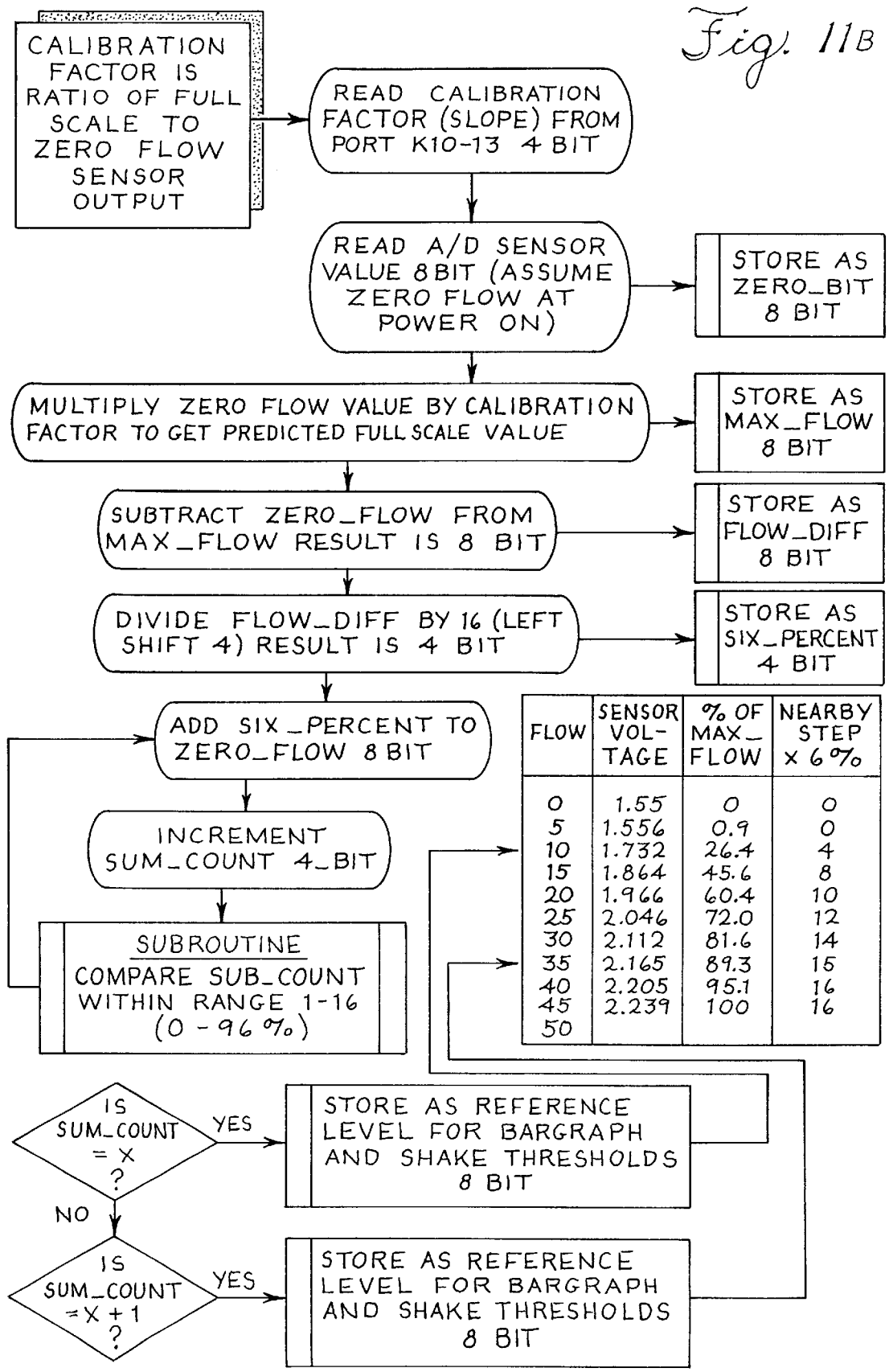
FIG. 11B shows a flow chart for determining the flow rate using the flow rate measurement devices of FIGS. 6–9.

An example of the flow rate or flowage measured by the flow rate measurement devices of FIGS. 6–9 is shown in FIG. 11a. It is believed that the specific curve in FIG. 11A will shift up or down during the life of the measurement devices, but the shape (gain) of the curve will remain the same. In each of the embodiments of FIGS. 6–9, the flow rate or flowage in the exhaust port 220 is determined by applying the steps shown in the flow chart of FIG. 11b that are carried out by the microprocessor 602, such as a 4-bit microcontroller. It is predicted that the ratio of the voltage signal, Vmax, generated by the sensor 308 at maximum flowage where the vane 302 is at maximum deflection to the voltage signal Vmin where the vane 302 is at the rest position is a constant K at all times. The constant K is preferably measured at the time of manufacture or calibration of the flow rate measurement device 300 and is stored in a memory of the microprocessor 602. During operation of the flow rate measurement device 300, the voltage signal Vrest generated by the vane 302 being at the rest position when the device 300 is first turned on is fed to and stored in the microprocessor 602. The microprocessor 602 calculates and stores the predicted voltage Vmaxdef for maximum deflection of the vane 302 by determining the value of the multiplicative product of K times the stored value of Vrest. Next, the full range of voltages that can be measured from no deflection to maximum deflection is determined by subtracting the voltage Vrest for the rest position from the calculated voltage Vmaxdef for maximum deflection. This subtraction also reduces the effect on the voltage of such factors as manufacturing tolerances and temperature. The full range of voltages is then divided into seven sub-ranges, where each sub-range corresponds to one of the seven bar graphs on the flow rate display 604 of the monitoring device 600. The sub-ranges are determined by first incrementing the voltage Vrest in sixteen steps that equal six percent of the full range of voltages. The flow rate for each increment is then compared with five subranges of flow rates where the subrange of flow rate that corresponds to the increment is displayed on display 606 as shown in FIGS. 14–15. An example of the sub-ranges of the flow rate display 604 is given FIGS. 11B and 15 and in the table below:

| Flow | Sensor Voltage | % of Full Range Voltage | Nearby step × 6% |
| --- | --- | --- | --- |
| 0 | 1.55 | 0 | 0 |
| 5 | 1.556 | 0.9 | 0 |
| 10 | 1.732 | 26.4 | 4 |
| 15 | 1.864 | 45.6 | 8 |
| 20 | 1.966 | 60.4 | 10 |
| 25 | 2.046 | 72.0 | 12 |
| 30 | 2.112 | 81.6 | 14 |
| 35 | 2.165 | 89.3 | 15 |
| 40 | 2.205 | 95.1 | 16 |
| 45 | 2.239 | 100 | 16 |

The full range of voltages and the sub-ranges are preferably recalculated with each use. It is understood that the resolution of the sub-ranges can be increased or decreased by altering the size of the incremental steps so that a desired resolution can be achieved. One possible set of sub-ranges is: less than 15 l/min, 15–25 l/min, 25–35 l/min, 35–40 l/min, 40–45 l/min, 45–50 l/min and greater than 50 l/min where the upper and lower ranges are unacceptable flow rates.

C. Shake Sensor

Besides measuring the flow rate, the moving vane 302 can be adapted to be a shake sensor 400. This is accomplished by adding a mass 402 to either of the vanes 302 shown in FIGS. 6–9. As shown in FIG. 9A, the mass 402 is attached to the upper section 306 by an adhesive so that it is centered at approximately 0.9 cm from the free end 318 of the vane 302 and 0.675 cm from either of the side edges 320. The mass 402 has an annular shape with a thickness of approximately 0.2 cm, an inner radius of approximately 0.15 cm and an outer radius of approximately 0.4 cm. The mass 402 preferably is made of stainless steel and has a mass of approximately 0.41 grams. The mass 402 performs the function of increasing the amount of force needed to affect acceleration thereby causing greater deflection of the vane 302 which can be more easily measured.

With the mass 402 attached to the vane 302, the voltage signal generated by the magnetic sensor 308 is processed by the microprocessor 602 so as to measure differential changes in the position of the vane 302 when the housing 202 is shaken or agitated. Measuring the differential changes allows the microprocessor to measure the acceleration of the housing 202. As shown in the flow chart of FIG. 12, the measured differential changes are compared with a predetermined differential change value that is stored in the microprocessor 602. A typical value of the stored predetermined differential change value would be 2.5 times the acceleration of gravity (g=9.8 m/s/s). The stored predetermined differential change value is representative of an acceptable acceleration caused by one shake of the container 204. During the comparison stage, the microprocessor 602 determines whether the measured differential change is above or below the predetermined differential change value. If it is above, a counter is incremented by one to register that a single adequate shake has been performed. In addition, a beep is generated signaling that the shake was adequate and indicating that another shake should be performed. The second shake is performed and the comparison with the predetermined differential change value is repeated. If the shake is acceptable, then the counter is incremented another step and a second beep is generated indicating the second shake was acceptable and that a third shake should be performed. The above process is continued until eight consecutive adequate shakes are performed where the microprocessor 602 signals, via display 604, that the container 204 is properly shaken and the next step of inhaling is to be attempted by the user. If an inadequate shake is performed at any time before reaching eight consecutive adequate shakes, then the counter is reset to zero and the user must start over and attempt to do eight consecutive adequate shakes in the manner described above.

Note that during each shake the value of the counter is compared with a stored number, such as eight, representative of the minimum number of shakes to properly mix the contents of the container 204 for consumption by a user.

As can be seen above, the signal generated by the vane 302 can be used by the microprocessor to measure a number of quantities, such as the position of the vane, the acceleration of the vane, the position of the vane in time, etc., and so can be used to generate other useful quantities, such as peak flow rate, to monitor the use of the device 200.

A second embodiment of a shake sensor is shown in FIG. 5. In particular, a shake sensor 400 is attached to the exterior side of the housing 202. The shake sensor 400 is in the shape of a cylindrical tube 404 having a radius of approximately 6 mm and a height of approximately 10 mm. The top end of the shake sensor 400 is capped off and the bottom end of the shake sensor 400 has a flexible contact surface 406 attached thereto so as to enclose the cylindrical tube 404. The contact surface 406 is circular in shape and is preferably made of plated copper.

Inside of the cylindrical tube 404 is ambient air. A contact member, such as the spherical ball 408, is placed in the tube 404 as well. The ball 408 is preferably made of steel, has a radius of approximately 3 mm, and has a mass of approximately 100 grams.

The shake sensor 400 operates as follows: The housing 202 and the container 204 are agitated or shaken. Since the tube 404 is attached to the housing 202, the tube 404 and the ball 408 are also shaken and moved in response to the shaking of the housing 202 and the container 204. A measure of the amount of agitation is the number of times that the ball 408 contacts the contact surface 406. Each contact between the ball 408 and the contact surface 406 is detected by a transducer or sensor 410 that is attached to the exterior side of the contact surface 406.

The signal generated by the sensor 410 is sent to the microprocessor 602 where it is processed in the same manner as the signal generated by the sensor 308 of FIGS. 2–4 and 6–9. To summarize, the signal is compared with a predetermined value indicative of an acceptable shake or agitation. The number of acceptable shakes or agitations is counted and compared with the previously described stored number representative of the minimum number of shakes or agitations to properly agitate and mix the contents of the container 204 for consumption by a user. If the number of measured shakes or agitations is below the stored number, then a signal or beep is generated by the microprocessor 602 that another shake or agitation is required. This process is continued until the stored number is reached where the microprocessor 602 signals that the container 204 is properly shaken or agitated and the next step of inhaling is to be attempted by the user. If an inadequate shake is performed at any time before reaching eight consecutive adequate shakes or agitations, the user must start over and attempt to do eight consecutive adequate shakes or agitations in the manner described above.

D. Actuation Sensor

As previously described, the flow rate measurement devices 300 and the shake sensors 400 are used to measure whether the magnitude of the flow rate within the exhaust port 220 and the agitation of the container 204 are adequate for using an aerosol dispensing device. Another important function of the aerosol dispensing inhaler training device 100 is to test the timing of the dispensing process, such as the shaking of the container 204 and the inhalation of the aerosol. To this end, an initiation or activation sensor 500 is used to detect when a portion of the propellant and the placebo within the container 204 is dispensed into the exhaust port 220 for inhalation.

The actuation sensor 500 is attached to the bottom of the housing 202 so as to be located within the housing 202 and directly below either the well 214 (FIGS. 2–4) or the top surface of the container 204 (FIG. 5) The actuation sensor 500 is a conventional contact sensor, such as a membrane switch. The sensor 500 can be protected from the environment by placing a thin plastic, such as polyester, over the sensor 500.

When the container 204 is not moved, the top surface of the container 204 is spaced above the sensor 500 and the bottom of the housing 202. When the bottom end of the container 204 is depressed it moves the valve system 228 to the open position that results in the dispensing of a portion of the placebo into the exhaust port 220. When the valve is first opened, the top surface of the container 204 (FIG. 5) or the bottom of the movable well 214 (FIGS. 2–4) first makes contact with the sensor 500. This results in the generation of a signal that is representative of the time when the housing 202 or the movable well 214 is moved to an actuation position where the valve stem is first opened and actuated so that the placebo is dispensed in an aerosol form. This signal is sent to the microprocessor 602 which then determines whether or not the timing of the operation of the aerosol dispensing device is proper. An explanation of the processing of the signal is discussed in the section below.

E. Monitoring Device and Training Procedure

Figure 12:
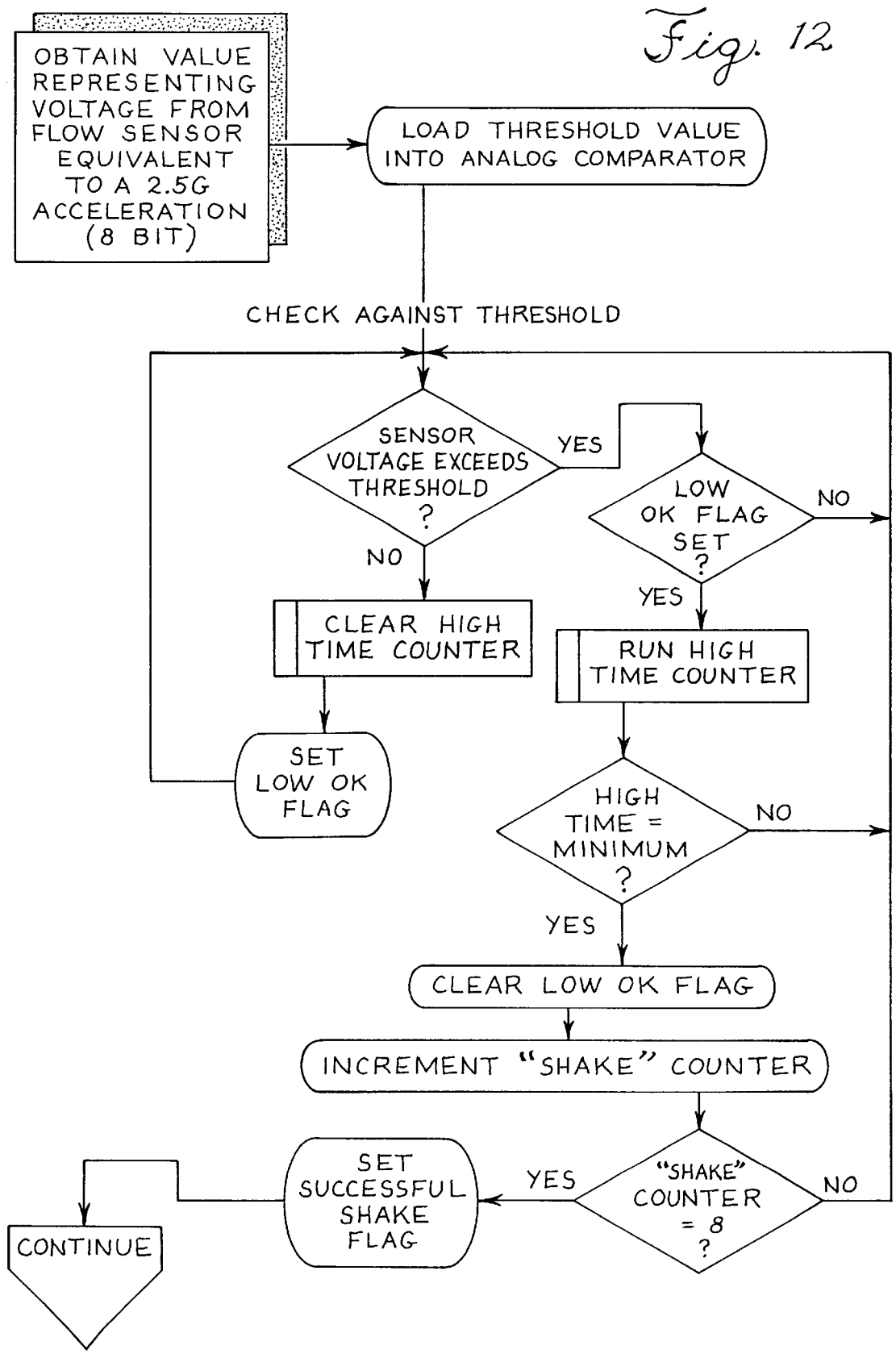
FIG. 12 shows a flow chart for determining proper shaking of the container of FIGS. 2–5.

As described above, the three signals from the flow rate measurement devices 300 of FIGS. 6–9, the shake sensors 400 of FIGS. 2–5 and the actuation sensor 500 are sent to the microprocessor 602 residing in the monitoring device 600 as shown in FIG. 12 (in the case of the shake sensor and the flow rate measurement devices being incorporated in the same vane 302, the shake sensor box can be eliminated). The monitoring device 600 monitors itself and processes the signals so that a user of the aerosol dispensing device 200 can learn how to properly use the device 200 and dispensing devices like it. In particular, once the monitoring device 600 is switched on, it runs a testing program that goes step-by-step through the process of using the device 200 while using the signals from the sensors to determine if a step has been successfully completed. The program monitors the completion or failure of a step to determine whether the testing should proceed or should be repeated. The program also informs the microprocessor which sensors or measurements are being measured.

The monitoring device 600 is preferably powered by two AA alkaline batteries so as to be portable. Of course it is possible to use other power sources without departing from the spirit of the invention. Once the monitoring device 600 is turned on by pushing the ON-OFF switch 604, the liquid crystal display (LCD) 606 is lit up so as to show several pictures as shown in FIGS. 1 and 14. Upon being turned on, the microprocessor 602 monitors the batteries and displays the remaining power in the batteries via the display of a battery A. As the batteries become weaker, the interior 608 of the displayed battery A will become lower and lower so as to indicate that new batteries will be needed. Besides monitoring the batteries, the microprocessor 602 checks if the other sensors are working properly. If so, a check mark B is displayed (see screen of FIG. 16A), and if not, the check mark B and a slash C are displayed simultaneously (see screen of FIG. 16B).

Figure 16A:
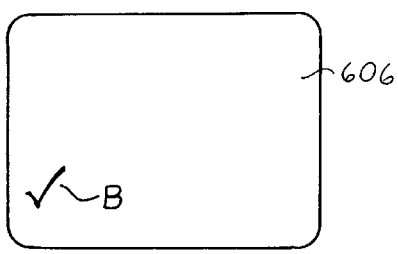
FIGS. 16A–G schematically show several display screens shown during the testing of a user.
Figure 16B:
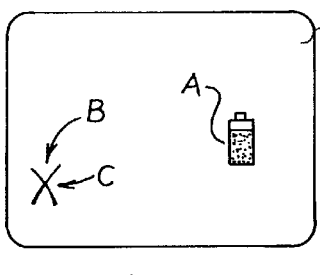
Figure 16C:
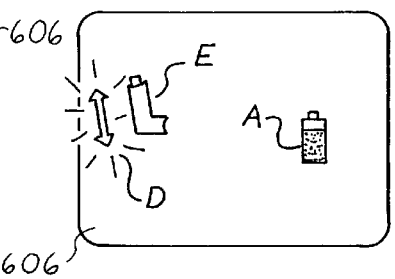

Assuming that the monitoring device 600 is in proper running order and check mark B is displayed, the display 606 will flash the arrow D near the picture of the dispensing device E (see FIG. 16C). The flashing arrow D alerts the user to attempt to adequately shake the container 204 eight consecutive times. A beep will be emitted by a speaker 608 after every successful shake. No beep will be generated if the shake is unsuccessful. The lack of a beep also indicates that the user must start from the beginning and attempt to achieve the eight consecutive adequate shakes.

When eight consecutive adequate shakes are achieved, the display 606 changes. First, it shows a clear screen with a check mark B (FIG. 17E) indicating the stage has been successfully completed and then it changes to a screen showing a trachea F connected to a pair of lungs G (see FIG. 16D). Flashing dots are shown in the trachea F. A vertical bar graph H and up and down arrows I and J are also displayed. This signals the user to place his or her mouth over the mouthpiece 216 and practice inhaling. By inhaling, the vane 302 will be moved. As described previously, the signal generated by the sensor 308 is representative of the flow rate. The microprocessor 602 compares the measured inhalation flow rate with two stored values representing the high end and low end of acceptable inhalation flow rates. If the measured flow rate is below the stored low end value, then the up arrow I will flash and a high frequency of beeps will be generated to alert the user to increase the flow rate. If the measured flow rate is above the stored high end value, then the down arrow J flashes and a low frequency of beeps is heard to warn the user to decrease the flow rate.

Once an acceptable inhalation flow rate is achieved, a beep will occur and a new screen showing a check mark B (FIG. 17E) will be shown on the display 606. Next, a new screen is shown that alerts the user that the inhalation of the placebo aerosol will be tested next As shown in FIG. 16E, a flashing finger K is displayed near the dispensing device E. The flashing finger K is a cue for the user to depress the container 204 while maintaining the inhalation performed during the step represented by the screen of FIG. 16D. Upon depression of the container 204, the placebo is dispensed into the exhaust port 220. The container 204 (FIG. 5) or the bottom of the movable well 214 (FIGS. 2–4) contacts the actuation sensor 500 which results in a signal being sent to the microprocessor 602 and the call up of the screen of FIG. 16F onto the display 606. If the user does not continue inhaling when activating the container 204, then the screen of FIG. 17D will show up on the display 606. Note that the screen of FIG. 16F will also be called up if the container 204 is not pressed within two seconds of the call up of the screen of FIG. 16E. Note that the screen of FIG. 16F will include an "X" that signifies a failed attempt.

Figure 16D:
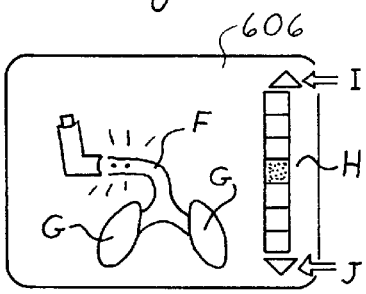
Figure 16E:
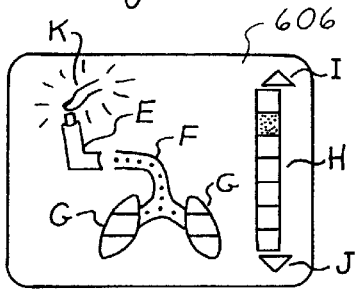
Figure 16F:
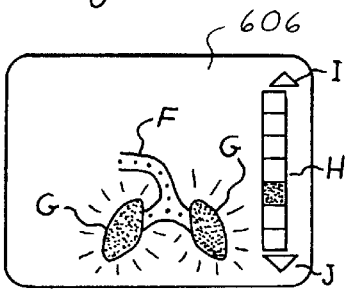
Figure 16G:
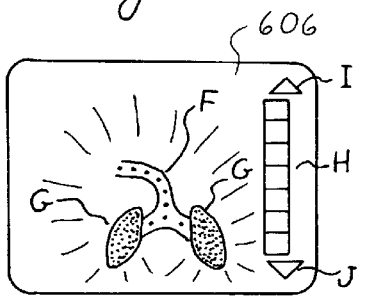
Figure 17A:
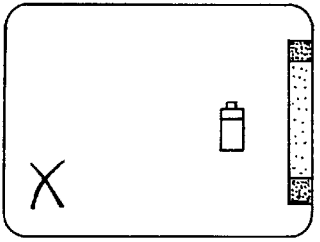
FIGS. 17A–E schematically show additional display screens shown during the testing of a user.
Figure 17B:
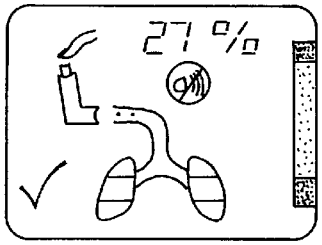
Figure 17C:
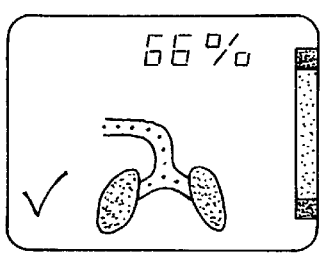
Figure 17D:
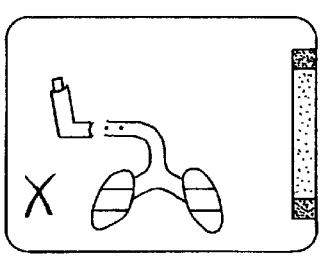
Figure 17E:
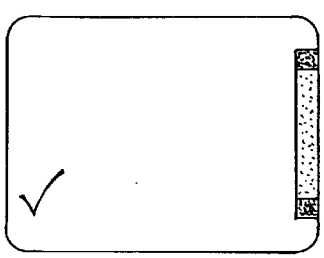

When the screen 16F is called up, the patient should still be performing the inhalation begun with the screen of FIG. 16D. The microprocessor 602 monitors the flow rate signals from the vane 302 and measures the flow rate from those signals. If the measured flow rate is maintained for two seconds within the range represented by the middle five green bars of the bar graph H (see FIG. 15), then a check mark is displayed (FIG. 17E). Next, another new screen (see FIG. 16G) is displayed where the lungs G and trachea F flash for five seconds to remind the user to hold his or her breath for the same five seconds. If the measured flow rate is not maintained for the first second then the user is given an additional second to achieve an acceptable flow rate. If an unacceptable flow rate is not achieved during the two second period, then a failure signal is shown and heard and the user is sent back to the shake step. If an acceptable flow rate is achieved in the second one second interval, a signal is displayed and a beep sounds indicating the attempt was unsuccessful and that the user should repeat the attempt of inhaling properly for two seconds.

The monitoring device 600 has several other features. For example, if the batteries need replacing, then the screen of FIG. 17A is shown on the display 606.

It is possible to review a user's test results at different stages of the testing process. This is done by pressing the memory button 608. Pressing the button 608 once results in a display of the number of tests attempted and the percentage that were successful. Two presses causes a display like FIG. 16D with the percentage of times that the inhaling at that stage was successful. Three presses results in a display like FIG. 17C where the percentage displayed is the percentage of times the container 204 was successfully actuated. A fourth press causes a display like FIG. 17D where the percentage displayed is the percentage of tests that the user inhaled the placebo aerosol at the proper flow rate for two seconds. A fifth press returns the screen to that of FIG. 16C.

Although the present invention has been described with reference to preferred embodiments, those skilled in the art will recognize that changes may be made in form and detail without departing from the spirit and scope of the invention. For example, the present invention can be used to diagnose or monitor a patient's pulmonary condition. In addition, the present invention is equally applicable to triggering the activation of various aerosol delivery devices, such as metered dose inhalers or nebulizers and can be used to train patients to inhale other products properly, such as dry powders. It is understood that depending on the type or delivery device or product inhaled, that the microprocessor 602 will need to be reprogrammed to test for parameters that will indicate proper usage of the device and/or proper inhalation of the product. It is contemplated, though, that the testing and monitoring for the new device or inhalation product will be similar to that described above. With the above comments in mind, it is intended that the foregoing detailed description be regarded as illustrative rather than limiting and that it is the appended claims, including all equivalents thereof, which are intended to define the scope of the invention.

We claim:

1. An aerosol dispenser comprising:
    a container comprising an interior;
    a shake sensor positioned within an interior of said aerosol dispenser, said shake sensor comprises a contact member and a contact surface, wherein said contact member moves in response to movement of said container and said shake sensor determines the number of times said container is shaken and whether the contents of said interior of said container have been properly agitated for consumption by a user.

2. The aerosol dispenser of claim 1, wherein said shake sensor detects the number of times said contact member contacts said contact surface.

3. The aerosol dispenser of claim 1, wherein said shake sensor comprises a cylindrical tube wherein said contact surface is attached to an end of said cylindrical tube.

4. The aerosol dispenser of claim 3, wherein said contact surface is circular and encloses said end of said cylindrical tube.

5. The aerosol dispenser of claim 3, wherein said contact member comprises a spherical ball positioned within said cylindrical tube.

6. The aerosol dispenser of claim 4, wherein said contact member comprises a spherical ball positioned within said cylindrical tube.

7. The aerosol dispenser of claim 1, wherein said shake sensor comprises a transducer attached to said contact surface.

8. The aerosol dispenser of claim 3, wherein said shake sensor comprises a transducer attached to said contact surface.

9. An aerosol dispensing inhaler training device for determining whether a user is properly operating an aerosol dispensing device, said aerosol dispensing inhaler training device comprising:
    an aerosol dispensing device comprising:
        a container comprising a valve stem extending longitudinally therefrom and movable between a closed position and an open position, said container dispensing a portion of the contents within said container when said valve stem is moved to the open position; and
        a housing adapted to support said container reciprocally moveable within said housing along a longitudinal axis from a first position, said housing comprising a well adapted to receive said valve stem and an exhaust port comprising one end in fluid communication with said well and a second end in fluid communication with the ambient atmosphere, wherein said portion of said contents within said container is dispensed from said first end of said exhaust port to said second end of said exhaust port when said housing moves to an actuation position where said valve stem is actuated so that a portion of said contents within said container is dispensed through said second end of said exhaust port when said valve stem is moved to the open position;
    a flow measurement device comprising a movable vane attached to said housing and located within said housing,
    a flow sensor that generates a first signal corresponding to the amount of movement of said movable vane; and
    a shake sensor positioned within said interior of said container, said shake sensor, wherein said shake sensor comprises a contact member and a contact surface, wherein said contact member moves in response to movement of said container and said shake sensor determines whether said contents within said container have been properly agitated for consumption by a user.

10. The aerosol dispensing inhaler training device of claim 9, wherein said shake sensor detects the number of times said contact member contacts said contact surface.

11. An aerosol dispensing inhaler training device for determining whether a user is properly operating an aerosol dispensing device, said aerosol dispensing inhaler training device comprising:
    an aerosol dispensing device comprising:
        a container comprising a valve stem extending longitudinally therefrom and movable between a closed position and an open position, said container dispensing a portion of the contents within said container when said valve stem is moved to the open position; and
        a housing adapted to support said container reciprocally moveable within said housing along a longitudinal axis from a first position, said housing comprising a well adapted to receive said valve stem and an exhaust port comprising one end in fluid communication with said well and a second end in fluid communication with the ambient atmosphere, wherein said portion of said contents within said container is dispensed from said first end of said exhaust port to said second end of said exhaust port when said housing moves to an actuation position where said valve stem is actuated so that a portion of said contents within said container is dispensed through said second end of said exhaust port when said valve stem is moved to the open position;
    an actuation sensor that generates a second signal that indicates when said housing is moved to said actuation position and said valve stem is actuated; and a shake sensor, wherein said shake sensor comprises a contact member and a contact surface, wherein said contact member moves in response to movement of said container and said shake sensor determines the number of times said container is shaken and whether said contents within said container have been properly agitated for consumption by a user.

12. The aerosol dispensing inhaler training device of claim 11, wherein said shake sensor detects the number of times said contact member contacts said contact surface.

13. An aerosol dispensing inhaler training device for determining whether a user is properly operating a aerosol dispensing device, said aerosol dispensing inhaler training device comprising:

an aerosol dispensing device comprising:
  a container comprising a valve stem extending longitudinally therefrom and movable between a closed position and an open position, said container dispensing a portion of the contents within said container when said valve stem is moved to the open position; and
  a housing adapted to support said container reciprocally moveable within said housing along a longitudinal axis from a first position, said housing comprising a well adapted to receive said valve stem and an exhaust port comprising one end in fluid communication with said well and a second end in fluid communication with the ambient atmosphere, wherein said portion of said contents within said container is dispensed from said first end of said exhaust port to said second end of said exhaust port when said housing moves to an actuation position where said valve stem is actuated so that a portion of said contents within said container is dispensed through said second end of said exhaust port when said valve stem is moved to the open position;
  a flow measurement device comprising a movable vane attached to said housing between said first end and said second end of said exhaust port,
  a flow sensor that generates a first signal corresponding to the amount of movement of said movable vane;
  an actuation sensor that generates a second signal that indicates when said housing is moved to said actuation position and said valve stem is actuated; and
  a shake sensor positioned within said interior of said container, wherein said shake sensor comprises a contact member and a contact surface, wherein said contact member moves in response to movement of said container and said shake sensor determines whether said contents within said container have been properly agitated for consumption by a user.

14. The aerosol dispensing inhaler training device of claim 13, wherein said shake sensor detects the number of times said contact member contacts said contact surface.

* * * * *

UNITED STATES PATENT AND TRADEMARK OFFICE
CERTIFICATE OF CORRECTION

PATENT NO. : 6,358,058 B1
DATED : March 19, 2002
INVENTOR(S) : John P. Strupat et al.

It is certified that error appears in the above-identified patent and that said Letters Patent is hereby corrected as shown below:

<u>Column 14,</u>
Line 29, delete "container, said shake sensor," and substitute -- container, -- in its place.

Signed and Sealed this

Twenty-first Day of January, 2003

JAMES E. ROGAN
*Director of the United States Patent and Trademark Office*